United States Patent [19]

Huang et al.

[11] Patent Number: 4,814,423
[45] Date of Patent: Mar. 21, 1989

[54] DUAL BONDING ADHESIVE COMPOSITION

[75] Inventors: Chin-Teh Huang, Dover; Steven R. Jefferies, Milford, both of Del.

[73] Assignee: Dentsply Research & Development Corp., Milford, Del.

[21] Appl. No.: 118,373

[22] Filed: Nov. 6, 1987

[51] Int. Cl.$^4$ ............................................. C08G 10/02
[52] U.S. Cl. ..................................... 528/230; 528/244; 528/245.3; 528/246; 523/115; 523/116; 523/118; 523/120
[58] Field of Search ............... 523/118, 115, 116, 120; 528/230, 244, 245.3, 246

[56] References Cited

U.S. PATENT DOCUMENTS

| | | | |
|---|---|---|---|
| 2,808,391 | 10/1957 | Pattison | 528/75 |
| 3,499,852 | 3/1970 | Schroeder et al. | 528/45 |
| 4,148,988 | 4/1979 | Masuhara et al. | 526/318 |
| 4,189,365 | 2/1980 | Schmitt et al. | 204/159.23 |
| 4,222,780 | 9/1980 | Shibatani et al. | 106/35 |
| 4,259,117 | 3/1981 | Yamouchi et al. | 106/35 |
| 4,368,043 | 1/1983 | Yamouchi et al. | 433/217 |
| 4,407,984 | 10/1983 | Ratcliffe | 523/115 |
| 4,409,332 | 10/1983 | Jefferies et al. | 435/188 |
| 4,421,894 | 12/1983 | O'Connor et al. | 525/28 |
| 4,437,836 | 3/1984 | Schmitz-Josten et al. | 433/199 |
| 4,452,964 | 6/1984 | Saracsan | 528/75 |
| 4,457,818 | 7/1984 | Denyer et al. | 204/159.19 |
| 4,459,193 | 7/1984 | Ratcliffe et al. | 204/159.23 |
| 4,483,759 | 11/1984 | Szyche et al. | 204/159.24 |
| 4,499,251 | 2/1985 | Omura et al. | 526/278 |
| 4,514,342 | 4/1985 | Billington et al. | 558/180 |
| 4,523,982 | 6/1985 | Lee | 204/159.15 |
| 4,537,940 | 8/1985 | Omura et al. | 526/278 |
| 4,539,382 | 9/1985 | Omura et al. | 526/276 |
| 4,544,467 | 10/1985 | Banker et al. | 204/159.24 |
| 4,593,054 | 6/1986 | Asmussen et al. | 523/118 |
| 4,612,384 | 9/1986 | Omura et al. | 558/198 |
| 4,636,533 | 1/1987 | Janda et al. | 522/14 |
| 4,640,936 | 2/1987 | Janda et al. | 522/14 |
| 4,650,847 | 3/1987 | Omura et al. | 526/376 |
| 4,698,376 | 10/1987 | Asmussen et al. | 523/115 |

OTHER PUBLICATIONS

Chemical Abstracts-CA, Pharmaceuticals 63, vol. 90, (1979), p. 395.
Munksgaard et al., Scand. J. Dent. Res. (1987); 95:185-190.

Primary Examiner—John Kight
Assistant Examiner—S. A. Acquah
Attorney, Agent, or Firm—David E. Wheeler; Edward J. Hanson, Jr.

[57] ABSTRACT

An adhesive for bonding polymeric material to both collagen and calcium is provided. The adhesive contains a glutaraldehyde component for bonding to collagen and a monophosphate component for bonding to calcium. It has been found that in bonding polymeric filling materials to teeth that the adhesive substantially reduces microleakage around the filling.

22 Claims, No Drawings

DUAL BONDING ADHESIVE COMPOSITION

BACKGROUND OF THE INVENTION

The present invention relates to an adhesive composition that bonds to collagen and to calcium.

PRIOR ART

Billington et al, in U.S. Pat. No. 4,514,342 teach polyethylenically unsaturated monophosphates that are useful as adhesives in bonding composite dental material to tooth enamel.

Asmussen et al, in U.S. Pat. No. 4,593,054 teach an adhesive promoting agent for bonding acrylate resins to collagen materials comprising a monomer of the acrylate type containing reactive hydrogen and an aldehyde.

Antonucci, in J. Dent. Res., Vol. 57 No. 3 (March 1978): "Aldehyde Methacrylate Derived from Hydroxybenzaldehydes," pp 500-505 teaches methacrylates having an aldehyde group for use as coupling agents for application on the interphase between dental filling compositions and hard tooth tissue such as dentin.

Blackwell et al, in U.S. Pat. No. 4,657,941 teach a biologically compatible adhesive that is a shelf stable single component adhesive which includes a mixture of an adhesive promoting a polymerizable monomer system having a free radical polymerizable monomer or prepolymer having ethylenic unsaturation and a phosphorous containing adhesion promoter.

BACKGROUND

In the treatment of cavities in teeth, the procedure used for many years is to remove decayed material from the tooth using, for example, a high speed drill, and to prepare the dental preparation formed by the drill to receive filling material therein by providing an undercut in the dental preparation, said undercut being used as a means for retaining the filling material in the dental preparation. Such a procedure requires the removal of a substantial amount of healthy tissue. In recent years, since the use of polymeric composite materials for filling teeth has become accepted, it has been found that, when an adequate adhesive is used, a composite material can be bonded to a tooth using only the adhesive, obviating the need for undercutting the dental preparation and removing substantial amounts of healthy tissue. Practitioners have found that such adhesives, and similar compositions can also be used to minimize microleakage around restorative fillings when the undercutting procedure for preparing a dental preparation is used.

There are two predominent mechanisms or systems used in dentistry for dentin bonding known in the art. One system uses an adhesive containing an active ingredient which acts to provide a bond with collagen. Examples of such adhesives are isocyanate compositions such as Dentin Adhesit ® available from Vivadent and gluteraldehyde/hydroxyethyl methacrylate containing compositions such as Gluma Dentin Bond available from Bayer. A second type of dentin adhesive uses a phosphate or other chelating agent as an adhesion promoter to provide calcium bonding. Examples of this second type of adhesive are Prisma Universal Bond ® available from L. D. Caulk division of Dentsply International Inc. and Scotchbond ® available from 3M Co.

Regardless of the type of adhesive used, it is often a problem in the art that when such adhesives are used to bond filling material in a tooth, when such material is used in the treatment of cavities, that biological material has a tendency toward microleakage around the filling material which eventually causes contamination of the dentin material of the tooth under the filling. Marginal gaps are frequently formed when restorative resins are used in dentin cavities due to the polymerization contraction of the resin. The use of dentin adhesives with composite filling material, to some extent, can minimize the marginal gaps. Although the problem of micro-leakage can be minimized, there is no means known in the art for substantially preventing such leakage from occuring. A bond between composite and dentin in a tooth is also stressed by contraction of the polymer filling material, by mastication forces and by temperature changes. Because there is a difference between the coefficient of thermal expansion of a tooth and composite material, temperatures above and below the setting temperature of the composite cause compressive and tensile forces on the bonds between the restoration and the tooth which could eventually cause the bond to break and permit percolation in the gap created between the filling and the tooth. Accordingly, it is a goal in the art to eliminate or at least to minimize as much as possible micro-leakage around filling materials in teeth.

It is an object of the present invention to provide an improved adhesive as well as to provide an adhesive with improved micro-leakage properties and to overcome other deficiencies in the prior art adhesives.

SUMMARY OF THE INVENTION

The invention relates to a dual bonding adhesive composition for bonding material to both collagen and calcium. The composition comprises an ethylenically unsaturated polymeric monophosphate, phosphate or phosphonate for bonding to calcium, and an aldehyde, hemi-acetal, blocked aldehyde (acetal), and an ethylenically unsaturated organic acid ester either separate or in the same molecule, for bonding to collagen. Preferably the aldehyde used in the composition, and the composition will be anhydrous. The composition preferably contains an initiator and accelerators which makes possible the curing of the composition using light in the visible wavelength range.

A method of bonding filling material to a tooth and substantially preventing leakage thereof is provided. The method comprises the steps of preparing the adhesive composition of the invention, preparing a tooth structure for filling thereof, coating the prepared tooth structure with the adhesive composition, and filling the tooth structure with said filling material. In the preferred embodiment, the method of the invention includes the step of curing the adhesive composition using actinic light in the visible wavelength range.

It has been found that the adhesive composition of the present invention provides superior adhesive properties while substantially eliminating micro-leakage penetration of the tooth structure. The adhesive is remarkably stable to thermal changes and to stress such as is encountered by mastication. The adhesive composition is easy to use in its preferred form since it is provided as a single component composition which is cured using light in the visible wavelength range. Since a one-component composition is used, the adhesive may be easily and inexpensively prepared and prepackaged at the factory in a form that is ready to use using inexpensive packaging. The composition is surprisingly stable and has a good shelf life. Since two components do not have to be mixed, chances of introducing air voids into the adhesive are minimized.

DETAILED DESCRIPTION OF THE INVENTION

The adhesive composition of the invention provides bonding to both collagen (i.e. organic peptide, proteins, etc.) and to calcium salt (i.e. hydroxappatite) of dentin. The component of the composition which is particularly adapted for bonding to calcium is an ethylenically unsaturated polymeric monophosphate, phosphate, or phosphonate. The component of the composition which adapts the composition for bonding to collagen is an aldehyde, blocked aldehyde (acetal) or hemiacetal. It is believed that the aldehyde, acetal or hemiacetal of the composition reacts with the organic phase(collagen) in such a way as to stabilize the system allowing the ethylenically unsaturated polymer of the monophosphate to bind the more effectively to the inorganic phase (hydroxy appatite). An ester of an ethylenically unsaturated organic acid may be added to the composition to enhance collagen bonding. It has been found that the composition combining the above mentioned components substantially eliminates micro-leakage when said composition is used to bond a filling material in a tooth, a property that is apparently not demonstrated by any of the adhesives known in the art.

As used herein, calcium is intended to refer to calcium ions in any form naturally occuring in the body, especially such ions as are present in bone or teeth structures.

As used herein the term phosphate may include monophosphates, diphosphates, etc., and phosphonates.

As used herein, aldehyde is intended to include chemical moiety which react chemically similar to aldehydes or can be converted into aldehydes in situ, such as, e.g. acetals and hemiacetals.

Microleakage may be defined as the percolation of oral fluids, especially bacteria or bacteria by-products, in the space that exists, if any, between restorative material and tooth structure.

The ethylenically unsaturated polymeric moiety of the monophosphate, phosphate or phosphonate may be a polyester, polyether or polyurethane and in its preferred embodiment will be the polymer of an unsaturated organic acid ester of 3 to 30 carbons and preferably 3 to 15 carbons.

The aldehyde used in the composition will preferably have 1 to 25 carbon atoms and more preferably 1 to 20 carbon atoms. The aldehyde may be aromatic or aliphatic and may be substituted by chemical groups that do not interfere with the activity of the aldehyde in the composition. Such substituents are exemplified but are not limited to halogens, amines, hydroxyl, heterocyclic rings, sulfhydryl, amines, amides, carboxyl, ether groups, ester groups, oxo, sulfonic acids and $NO_2$.

The aldehyde used in the composition may be in the form of a blocked aldehyde (acetal), or hemiacetal.

In the preferred embodiment, the ester of an ethylenically unsaturated organic acid will be added to the composition to enhance collagen bonding and will have 4 to 30 carbon atoms and may be in polymeric form. The ester will preferably have a substituent having a motile hydrogen. In the most preferred embodiment the ester will be the ester of acrylic or methacrylic acid containing an —OH, —$NH_2$ or —NH moiety.

As mentioned above, the adhesive of the invention may be prepared without the presence of a separate ester of an ethylenically unsaturated organic acid. In such an embodiment the polymeric portion of the polymeric monophosphate, phosphate or phosphonate will contain ethylenically unsaturated organic acid ester groups, and said groups in conjunction with the aldehyde, acetal or hemiacetal in the composition will provide bonding to collagen. It will be recognized by those skilled in the art that an aldehyde group may be present in the polymeric phosphate or phosphonate or in the ester of the unsaturated organic acid as part of the same molecule, and provide similar chemical activity to that obtained by an aldehyde added to the composition.

The adhesive of the present invention, which provides bonding to both calcium and collagen of dentin, demonstrates reduced microleakage more than could be predicted based on the separate measured microleakage of calcium and collagen bonding adhesive compositions alone.

Based on the results obtained with the adhesive of the invention it is believed that the molecular sized spaces ordinarily present between a tooth structure and filling material are occluded by the adhesive of the invention forming a more stable bond or network, thereby substantially preventing any micro-leakage from taking place.

The adhesive of the invention was prepaed with the goal of being stable to heat aging at 50° C. for at least one week. The adhesive of the invention was found to be stable to heat aging at 50° C. for two weeks as evidenced by tests for bond strength and micro-leakage.

The prior art composition used for collagen bonding is an aqueous solution comprising 5% glutaraldehyde and 35% hydroxyethylmethacrylate (HEMA). This solution is first applied to ethylene diamine tetraacetic acid(EDTA) treated dentin followed by a conventional bonding agent and restorative. In microleakage tests, this system provided leakage results of 0.7–0.96. Quantification of microleakage is determined as described by Hammesfahr et al in Dental Materials, Vol. No. 3, no. 4, Aug. 1987, pp. 194–199.

By contrast, in the adhesive of the invention, an anhydrous aldehyde is used in the non-aqueous resin based adhesive composition of the invention and the concentration of glutaraldeyde and HEMA used in the adhesive are only 0.3–0.6% and 2.2–4.4% respectively and yet provides leakage results with a value in the range of about 0.02 to 0.50. Thus, the amount of aldehyde and HEMA used in the adhesive was reduced by 10 fold in the non-aqueous systems and better results were achieved as compared to the prior art aqueous adhesive. Further there is no requirement for a separate resin bonding agent as the adhesive composition of the present invention contains an unsaturated bonding resin. Pretreatment of dentin with EDTA using the adhesive of the invention is believed to be contraindicated as the EDTA tends to deplete the dentin surface of inorganic materials such as calcium, to which the phosphate of the adhesive of the invention is designed to bond. Unexpectedly, the microleakage of this adhesive is better than either the prior art collagen bonding adhesive or calcium bonding adhesive alone. The bond strengths to dentin of the adhesive of the invention yield values similar to those of calcium bonding adhesives, and improved values over collagen bonding adhesives.

Exemplary aldehydes that have been found to be suitable for use in the adhesive composition of the invention include, but are not limited to formaldehyde, a compound which is able to release formaldehyde, acetaldehyde, propionaldehyde, butyraldehyde and glutaraldehyde.

In the preferred embodiment the aldehyde used is glutaraldehyde and the ester of an ethylenic unsaturated organic acid used is hydroxyethylmethacrylate.

The ethylenically unsaturated polymeric monophosphate used in the adhesive composition may be a polyester monophosphate, a polyether monophosphate or a polyurethane monophosphate.

In the preferred embodiment, the ethylenically unsaturated polymeric monophosphate has the formula

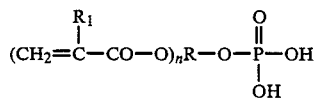

and salts thereof in which:

R is a pentaerythritol radical containing from 4 to 16 carbon atoms;

$R_1$ is a hydrogen atom, alkyl of 1 to 3 carbon atoms, halogen or —CN, and n is an integer of at least 3.

More preferred are the compositions defined above where $R_1$ is H or methyl; and n is an integer of from 3 to 6.

In the most preferred embodiments, the ethylenically unsaturated polymeric monophosphate used in the composition will be selected from the group comprising pentaerythritol triacrylate monophosphate, pentaerythritol trimethacrylate monophosphate, dipentaerythritol pentaacrylate monophosphate, dipentaerythritol pentamethacrylate monophosphate and mixtures thereof.

The adhesive composition of the invention comprises an elastomeric resin, hydroxyalkyl substituted dimethacrylate, hydroxyaryl substituted dimethacrylate, ethylenically unsaturated polymeric phosphoric acid ester, N-alkyl substituted methacrylate, aldehyde of 1–20 carbon atoms, hydroxy alkyl substituted methacrylate and at least one catalyst and at least one accellerator.

In the preferred embodiment the adhesive composition comprises a urethane elastomeric resin, triethylene glycol dimethacrylate (TEGDMA), bisphenol-A-dimethacrylate, dipentaerythritol penta acrylate phosphoric acid ester (PENTA), 2-N-morpholinoethyl methacryltte, camphorquinone, lithium toluene sulfinate, butylated hydroxy toluene (BHT), glutaraldehyde, and hydroxy ethylmethacrylate.

The preferred urethane elastomeric resin of the invention (and the one used in the examples described below) is the reaction product of trimethyl hexamethylene diisocyanate with polytetramethylene ether glycol; capped with hydroxy ethyl methacrylate. The resin is formed using stannous octoate as a catalyst.

The resin used in the preferred embodiment of the adhesive of the invention is made in accordance with the following Example:

Preparation of Anhydrous Glutaraldehyde

To a stirred 150 ml of 25% aqueous glutaraldehyde solution, 33 g of sodium chloride and 100 ml ether were added and stirred for 15 minutes. The ethereal extract was separated and stored in a flask. The aqueous layer was further extracted twice with a portion of 100 ml ether as above. The combined ethereal extracts were stirred with 8 g anhydrous magnesium sulfate for ½ hour, filtered, and stripped on a rotary evaporator under vacuum to give 15.6 g oily product.

Preparation of PENTA

Dipentaerythritol Pentaacrylate Phosphoric Acid Ester (PENTA)

A solution of technical dipentaerythritol monohydroxypentaacrylate (1 mole) and triethylamine (1 mole) in dry ether was slowly added with stirring to a solution of phosphorus oxychloride (1 mole) in dry ether, at 0° C. After stirring for two hours at room temperature, the reaction mixture to ice water with stirring at below 10° C. The resultant mixture was separated and the separated ether layer was then extracted with a 25% aqueous sodium carbonate solution. The aqueous extract exhibited a PH of about 8. The alkaline aqueous extract was then acidified with 18% hydrochloric acid and an oily material was formed. The oily material was extracted with methylene chloride and the extract was dried over anhydrous sodium sulphate. The methylene chloride was then removed from the dried extract under reduced pressure to give the title compound as a clear straw-colored oil.

Preparation of Urethane Dimethacrylate (UDMA)

To a mechanically-stirred mixture of 28.59 weight parts of trimethylhexamethylene diisocyanate and 0.04 weight part of stannous octoate in a reactor and purged with dry air, there is added 44.80 weight parts of polytetramethylene ether glycol, while maintaining the reaction temperature at 50° to 60° C. After the addition is complete, the mixture is heated to 70° to 80° C. and held for 3 hours. A 26.58 weight parts of hydroxyethyl methacrylate (HEMA) was added and the mixture was stirred at 70° to 80° C. until the percent NCO assay was below 0.01%.

Preparation of Composition A

A mixture of 55.44 weight parts of UDMA, 27.77 weight parts of TEGDMA, 9.6 weight parts of Bisphenol A Dimethacrylate and 0.02 weight part of butylated hydroxy-toluene was heated in a reactor at 40° to 45° C. until a homogenous mixture was obtained. To this mixture, 4.73 weight parts of PENTA and 2.08 weight parts of N-morphlinoethyl methacrylate were added and mixed for ½ hour at 40° to 45° C. A mixture of 0.12 weight part of lithium p-toluene-sulfinate and 0.24 weight part of camphoroquinone was added to the above mixture and stirred for 1 hour at 40° to 45° C.

Preparation of Composition 1, 2, and 3

A general procedure for preparation of these compositions is described as follows:

| Materials | Composition - % Weight | | |
|---|---|---|---|
| | 1 | 2 | 3 |
| Composition A | 95.00 | 97.50 | 96.40 |
| Glutaraldehyde (Anhydrous) | 0.63 | 0.31 | 0.45 |
| HEMA | 4.37 | 2.19 | 3.15 |

A mixture of these three components were mixed with agitation at 40° to 50° C. until homogenous mixture was obtained.

The composition of an exemplary embodiment of the adhesive is as follows:

Composition of the adhesive of the invention

| Materials | % Wt. |
|---|---|
| Resin | 52.67 |
| TEGDMA | 26.38 |
| Bis-phenol A Dimethacrylate | 9.12 |
| BHT | 0.02 |
| PENTA | 4.49 |
| N—Morpholinoethyl Methacrylate | 1.98 |
| Lithium Toluene Sulfinate | 0.11 |
| Camphorquinone | 0.23 |
| Glutaraldehyde | 0.63 |
| Hydroxyethyl Methacrylate | 4.37 |
| Total | 100.00 |

The glutaraldehyde used in the composition is anhydrous. The anhydrous glutaraldehyde is prepared from a 25% aqueous solution which is extracted with an organic solvent. The glutaraldehyde is recovered by vacuum distillation from the organic solvent in a rotary evaporator.

Bond strengths to dentin, stability and microleakage were evaluated. Particularly, PRISMA UNIVERSAL BOND ® and the collagen adhesive described above were used as controls in the leakage testings. Stability was tested in a 50° C. oven for 1-week and 2-week periods. Procedure for the microleakage testing was as follows:

Microleakage Procedure

Extracted human molar teeth were cleaned and disinfected with a sodium hypochlorite solution (1% in water) as described above. The teeth were then stored in water until needed. Two non-retentive V-shaped, Class V cavities were prepared on opposite sides of each tooth, e.g., buccal and lingual surfaces, or mesial and distal surfaces, to provide a control as well as a test system. A No. 58 carbide bur at high speed with water colling was used to cut the preparation at the junction of the enamel and cementum so that half of the cavosurface margins were in enamel and half were in cemetum (dentin). A new No. 58 bur was used after five cavity preparations were cut. Approximate dimensions of the preparations were 4 mm masiodistally, 3 mm occluso-gingivally, and 2 mm pulpal. Each cavity was rinsed with water, then dried with compressed air with no additional treatment to the dentin surface prior to bonding unless specified by the manufacturer.

A group of at least five teeth were used for each experiment. Multiple replications of each experiment were necessary to ensure sufficient sample size for evaluation. The enamel wall only of the preparation was conditioned for 60 seconds with an acid gel (CAULK TOOTH CONDITIONER GEL*) which was applied with a small brush and left undisturbed for the prescribed time, followed by a 15-second rinse with an air-water mist. The preparations were then air-dried with a compressed, oil-free air stream for 10 seconds.

The following represent an example of the technique employed: The conditioned enamel and freshly cut dentin surface were coated with a uniform thin layer of an enamel/dentin adhesive, (PRISMA ® UNIVERSAL BOND ®). A small brush was used to place the adhesive and an air blast from a dental syringe was used to further thin the application and remove any excess adhesive. The adhesive was then cured for 10 seconds with a dental visible light polymerization unit (PRISMTICS LITE ®). A second application of the PRISMA UNIVERSAL BOND adhesive was placed with a small brush and thinned with an air blast. The second adhesive coat was also light polymerized for 10 seconds.

A light-cured composite (PRISMA-FIL ®, FUL-FIL ®) or light-cured microfilled resin (PRISMA ® MICRO-FINE) was placed in the preparation in one increment. Following bulk placement, the composite was cured for 30 seconds. The restorations were immediately finished with abrasive discs, (Soft-Lex TM 3M Company) coarse, medium, and fine. Following the finishing procedure the specimens were stored in water (distilled or tap) at 37° C. for 16–48 hours.

The teeth in each group were then thermocycled between a water bath of 48° C.±2° C. and 10° C.±2° C. for 24 hours (540 cycles). Immersion time was approximately one minute in each bath with transfer time of 13 seconds in air between baths. Following the thermocycling period, the teeth were evaluated for marginal microleakage by modification of a silver nitrate staining technique described by Wu, et al (16). Dental compound was placed in the intra-radicular areas, and the teeth were coated with fingernail polish up to within 2 mm of the restoration to prevent silver nitrate penetration into the teeth from areas other than the cavity preparation. In a darkened room, the teeth were placed in 50% (by wt.) silver nitrate aqueous solution, and stored in total darkness for two hours. The teeth were removed from the silver nitrate solution and rinsed in tap water. Following rinsing, the teeth were sectioned longitudinally with a diamond blade through the center of the restorations.

The development process consisted of exposure of each sectioned specimen to a photoflood lamp for five minutes. Areas of silver nitrate penetration (microleakage) turned black due to the light exposure. The degree of marginal microleakage along the gingival wall (dentin) was determined by the degree of penetration of silver nitrate stain.

Leakage along the gingival wall of the cavity was reported as the ratio of the depth of penetration along the wall to the total length of the wall from the cementum to the apex. For example, stain penetration one-half of the distance to the apex is 0.5, while leakage to the bottom (apex) of the cavity yields 1.0 as the leakage value. In the cases when penetration continues past the apex and is observed on the occlusal wall, the ratio is calculated in a similar manner to yield penetration values between 1.0 and 2.0. The procedure used to measure these ratios was performed with a microscope.

Bond strengths to dentin are shown in Table 1.

TABLE 1

| Bonding Agent* | Composite | Testing** Conditions | Bond Strengths (psi) × (S.D.) N |
|---|---|---|---|
| CTH2-109-7 | PRISMA-FIL | R.T. | 1,259 (316) 5 |
| CTH2-109-7 | PRISMA-FIL | After 1 wk. @ 50° C. | 1,606 (362) 5 |
| CTH2-109-7 | PRISMA-FIL | After 2 wks. @ 50° C. | 1,096 (504) 5 |

*CTH2-109-7 is composition 1
**For bonding agent

The microleakage results of the experimental dual-bonding agent, CTH2-109-7, versus PRISMA UNIVERSAL BOND ® (PUB), 041086, are summarized in Table 2.

TABLE 2

| Experiment | Composite | Leakage Value* CTH2-109-7 | PUB (041086) |
|---|---|---|---|
| CTH2-114-5 | P(MF) | 0.3 | — |
| CTH2-123-1 | P.F. | 0.04 | 0.36 |
| CTH2-126-2 | F.F. | 0.06 | 0.34 |
| CTH2-126-3 | P.F. | 0.20 | 0.44 |
| CTH2-123-4 | P.F. | 0.06** | 1.21 |

*Leakage value is measured along the gingival wall of the cavity. The test specimens were thermocycled 540 times between 10° C. to 50° C.
**The experimental bonding agent was aged at 50° C. for 2 weeks.

When the bonding agent, CTH2-109-7, was compared to the collagen adhesive described above in the microleakage test, the same composite, PRISMA-FIL, was used and the corresponding leakage value was 0.15 versus 0.96.

As can be seen from the above results, the experimental dual-bonding agent provides good bond strengths to dentin and superior microleakage performance as compared to those of PRISMA UNIVERSAL BOND ® and prior art collagen adhesives.

Three concentration levels of glutaraldehyde/HEMA were further examined for microleakage. These compositions are illustrated in Table 3. The modified Class V Vee-prep consisting of ½ enamel and ½ dentin and Standard Class II preparation were investigated. The leakage results are shown in Table 4.

As illustrated in Table 4, the average leakage value of 12 experiments including all three compositions is 0.20 as compared to an average of 0.75 for PUB with PRISMA-FIL as composite. In class II preparation, the result is in favor of the experimental adhesive as well. It is noted in Experiment CTH2-132-1 that the leakage result of the experimental adhesives is superior to prior art collagen adhesives described above. Similar improvements in microleakage are obtained when PRISMA MICRO-FINE and FUL-FIL are used as restorative material. The bond strength of this experimental adhesive to dentin provides similar results to those obtained for PUB, with demonstrated improvement in microleakage. It may be inferred from this that additional collagen bonding due to glutaraldehyde/HEMA is not as good as phosphate bonding; therefore, the upper limit of adhesion to dentin does not increase. However, the density of the bonding sites increases, and consequently the leakage of the experimental adhesive is reduced.

TABLE 3

| Materials | Composition 1 | Composition 2 | Composition 3 |
|---|---|---|---|
| PRISMA UNIVERSAL BOND ® | 95.0% Wt. | 97.499% Wt. | 96.40% Wt. |
| Glutaraldehyde (100%) | 0.625 | 0.313 | 0.45 |
| Hydroxyethyl Methacrylate | 4.375 | 2.188 | 3.15 |

TABLE 4

| Experiment | Composite | Bonding Agent | Location*1 of Prep | Leakage Value |
|---|---|---|---|---|
| CTH2-123-1 | P.F. | Composition 1 | A | 0.04 |
|  | P.F. | PUB*4 | B | 0.36 |
| CTH2-123-4 | P.F. | Composition 1*2 | A | 0.06 |
|  | P.F. | PUB | B | 1.21 |
| CTH2-126-3 | P.F. | Composition 1 | A | 0.02 |
|  | P.F. | PUB | B | 0.44 |
| CTH2-132-1 | P.F. | Composition 1 | A | 0.15 |
|  | P.F. | Gluma Bond | B | 0.96 |
| CTH2-132-2 | P.F. | Composition 2 | A | 0.27 |
|  | P.F. | PUB | B | 0.84 |

TABLE 4-continued

| Experiment | Composite | Bonding Agent | Location*1 of Prep | Leakage Value |
|---|---|---|---|---|
| CTH2-151-1 | P.F. | Composition 2 | A | 0.26 |
|  | P.F. | PUB | B | 0.55 |
| CTH2-151-2 | P.F. | Composition 1 | A | 0.1 |
|  | P.F. | Composition 2 | B | 0.1 |
| CTH2-151-3 | P.F. | Composition 1 | A | 0.24 |
|  | P.F. | Composition 2 | B | 0.48 |
| CTH2-151-4 | F.F. | Composition 3 | A | 0.15 |
|  | F.F | PUB | B | 0.45 |
| CTH2-126-2 | F.F. | Composition 1 | A | 0.06 |
|  | F.F. | PUB | B | 0.34 |
| CTH2-162-5 | P(MF) | Composition 3 | A | 0.10 |
|  | P(MF) | PUB | B | 0.40 |
| SRJ-1 | P.F. | Composition 3 | B | 0.31 |
|  | P.F. | PUB | A | 1.1 |
| JFF*3 | F.F. | Composition 3 | B | 0.5 |
|  | F.F. | PUB | A | 2.0 |

*1 A - Referring to unnotched side of teeth
B - Referring to notched side of teeth
*2 This Bonding Agent has been aged at 50° C. for two weeks.
*3 This experiment is a Class II preparation.
*4 PUB - PRISMA UNIVERSAL BOND ®

While present embodiments of the invention and methods of practicing the same have been illustrated and described, it will be recognized by those skilled in the art that this invention may be otherwise variously embodied and practiced within the scope of the following claims.

What is claimed is:

1. An adhesive composition for bonding to both collagen and calcium, comprising an ethylenically unsaturated polymerizable phosphate and an aldehyde.

2. The adhesive composition according to claim 1 in which said aldehyde is anhydrous.

3. The adhesive composition of claim 1 in which said aldehyde is an aldehyde substituent on said ethylenically unsaturated phosphate.

4. The adhesive composition according to claim 1 which includes an ester of acrylic or methacrylic acid.

5. The adhesive according to claim 4 in which said ester of acrylic or methacrylic acid contains an —OH, NH$_2$, or —NH moiety.

6. The adhesive composition according to claim 1 in which said aldehyde is selected from the group consisting of formaldehyde, a compound which is able to release formaldehyde, acetaldehyde, propionaldehyde, butyraldehyde and glutaraldehyde.

7. The adhesive composition according to claim 1 in which said aldehyde is glutaraldehyde and said ester is hydroxyethylmethacrylate.

8. The adhesive composition according to claim 1 in which said ethylenically unsaturated polymeric phosphate is a polyestermonophosphate.

9. The adhesive composition according to claim 1 in which said ethylenically unsaturated polymeric phosphate is a polyethermonophosphate, or a polyurethanemonophosphate.

10. The adhesive composition according to claim 1 in which said ethylenically unsaturated polymerizable monophosphate has the formula

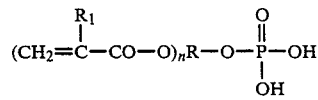

and salts thereof in which:

R is a pentaerythritol radical containing from 4 to 16 carbon atoms;

$R_1$ is a hydrogen atom, alkyl of 1 to 3 carbon atoms, halogen or —CN, and n is an integer of at least 3.

11. The adhesive composition according to claim 10 wherein $R_1$ is hydrogen or methyl; and n is an integer of from 3 to 6.

12. The adhesive composition according to claim 10 wherein said monophosphate is pentaerythritol triacrylate monophosphate.

13. The adhesive composition according to claim 10 wherein said monophosphate is pentaerythritol trimethacrylate monophosphate.

14. The adhesive composition according to claim 10 wherein said monophosphate is dipentaerythritol pentaacrylate monophosphate.

15. The adhesive composition according to claim 10 wherein said monophosphate is dipentaerythritol pentamethacrylate monophosphate.

16. The adhesive composition according to claim 1 which comprises a resin, hydroxyalkyl substituted dimethacrylate, hydroxy aryl substituted dimethacrylate, ethylenically unsaturated polymerizable phosphoric acid ester, N-alkyl substituted methacrylate, aldehyde of 1–20 carbons, hydroxy alkyl substituted methacrylate and at least one catalyst and at least one accelerator.

17. The adhesive composition according to claim 1 which comprises a urethane elastomeric resin, triethylene glycol dimethacrylate, bisphenol-A-dimethacrylate, dipentaerythritol penta acrylate phosporic acid ester, 2-N-morpholinoethyl methacrylate, camphorquinone, lithium toluenesulfinate, butylated hydroxy toluene, glutaraldehyde, and hydroxyethylmethacrylate.

18. The adhesive composition according to claim 1 which comprises by weight about 51–55% urethane elastomeric resin, about 23–29% triethylene glycol dimethacrylate, about 10–22% bisphenol-A-dimethacrylate, about 3–6% dipentaerythritol penta acrylate phosporic acid ester, about 1–3% 2-N-morpholinoethyl methacrylate, about 0.1–1% camphorquinone, about 0.1–1% lithium toluenesulfinate, about 0.02% butylated hydroxy toluene, about 0.05–1% glutaraldehyde, and about 2–5% hydroxyethylmethacrylate.

19. A method for bonding a filling material to a tooth and substantially preventing leakage thereof comprising the steps of
    (a) preparing one component light polymerizable adhesive comprising an ethylenically unsaturated polymerizable phosphate for calcium bonding and an aldehyde for collagen bonding
    (b) preparing a tooth structure for filling thereof
    (c) coating said prepared tooth structure with said adhesive, and
    (d) filling said tooth structure with a filling material.

20. The method according to claim 19 comprising the step of preparing said adhesive using an anhydrous aldehyde.

21. The method according to claim 19 comprising the step of preparing said adhesive using an ethylenically unsaturated polyestermonophosphate.

22. The use of the composition of claim 1 as a bone cement or a dental adhesive.

* * * * *